(12) United States Patent
Komai et al.

(10) Patent No.: US 6,255,478 B1
(45) Date of Patent: Jul. 3, 2001

(54) NUCLEIC ACID EXTRACTION METHOD

(75) Inventors: Shigeru Komai; Katsuya Daimon; Yutaka Takarada, all of Otsu (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/476,379

(22) Filed: Jan. 3, 2000

Related U.S. Application Data

(62) Division of application No. 09/241,242, filed on Feb. 1, 1999.

(30) Foreign Application Priority Data

Feb. 2, 1998 (JP) .................................... 10-21050

(51) Int. Cl.⁷ .......................... C07H 21/00; C07H 21/02; C07H 21/04; C12M 1/33
(52) U.S. Cl. ................. 536/25.4; 536/25.41; 536/25.42; 435/306.1
(58) Field of Search ................................ 536/25.3, 25.31, 536/25.4, 25.41, 25.42; 435/306.1

(56) References Cited

U.S. PATENT DOCUMENTS 5,538,849 * 7/1996 Uematsu et al. .
5,645,723 * 7/1997 Fujishiro et al. .

FOREIGN PATENT DOCUMENTS

| | | |
|---|---|---|
| 0 246 103 | 11/1987 | (EP) . |
| 0 487 028 | 5/1992 | (EP) . |
| 0 567 093 | 10/1993 | (EP) . |
| 0 638 809 | 2/1995 | (EP) . |
| 2 748 569 | 11/1997 | (FR) . |
| WO96/06850 | 3/1996 | (WO) . |
| 97 34908 | 9/1997 | (WO) . |
| 98 56506 | 12/1998 | (WO) . |

* cited by examiner

Primary Examiner—James O. Wilson
(74) Attorney, Agent, or Firm—Kenyon & Kenyon

(57) ABSTRACT

This invention provides an apparatus for extracting nucleic acids from nucleic acid-containing samples, particularly biological samples, and more particularly to a nucleic acid extraction apparatus well suited for the nucleic acid extraction method utilizing a nucleic acid-binding magnetic carrier. The nucleic acid extraction apparatus of the invention comprises (1) a group of extraction vessels each comprising a reactor tube in which a sample, a reagent solution, and a magnetic carrier are admixed and reacted, a drain cup for pooling an unwanted component solution, and a nucleic acid recovery tube all as secured to a support, (2) a distribution means for introducing a solution into each of the extraction vessels, (3) a stirring means for mixing the solution and magnetic carrier in the reactor tube, (4) a holding means for holding the magnetic carrier stationary within the vessel, (5) a discharging means for discharging the solution from the reactor tube while the magnetic carrier is held stationary, (6) a heating means for heating the solution and magnetic carrier in the reactor tube, and (7) a transfer means for serially transferring the vessels to the given positions where the distribution means, stirring means, holding means, discharging means and heating means are respectively disposed.

4 Claims, 16 Drawing Sheets

NUCLEIC ACID EXTRACTION METHOD

This is a division of application number 09/241,242 filed Feb. 1, 1999.

FIELD OF THE INVENTION

The present invention relates to an apparatus for extracting nucleic acids from various nucleic acid-containing samples, particularly biological samples. More particularly, the invention relates to a nucleic acid extraction apparatus well suited for a technology for extracting nucleic acids using a nucleic acid-binding magnetic carrier.

DESCRIPTION OF RELATED ART

The extraction of nucleic acids from biological or other samples is being practiced of late in many fields. For example, genetic engineering and construction of DNA probes in particular involve a procedure of extracting DNA or RNA coding for an objective protein from cells producing the protein. Moreover, the clinical examination for detecting a virus DNA or RNA using a DNA probe includes a procedure of extracting the target DNA or RNA from a biological sample.

The procedure of extracting nucleic acids is, thus, of great importance in various fields. The hitherto-known technology for extracting nucleic acids includes a method which comprises treating a sample with a caustic reagent, extracting the nucleic acid with phenol or phenol-chloroform, and recovering DNA by ethanol precipitation and a method which comprises treating a sample with a proteolytic enzyme such as proteinase K in the presence of a surfactant and then extracting the nucleic acid (Idenshi Kogaku [Genetic Engineering], Vol. 1, No. 1, p. 112–119, 1997), among others.

The vessel used conventionally in those extraction methods includes a group of plastic microtubes each provided with a cover as described in Unexamined Japanese Patent Publication No. 18362/1985 (Examined Japanese Patent Publication No. 31945/1992). This vessel is generally used with said cover kept open during the extraction procedure.

A variety of nucleic acid extraction apparatuses have been proposed according to the above nucleic acid extraction technology.

For example, Unexamined Japanese Patent Publication No. 125972/1991 describes a nucleic acid extraction apparatus designed to prevent viral infection and improve the efficiency of extraction which comprises a multiarticulated industrial robot and peripheral units necessary for DNA extraction and purification.

Unexamined Japanese Patent Publication No. 131076/1992 discloses an extraction apparatus designed to improve the efficiency of extraction of nucleic acids from a small amount of blood or other biological material through a compact arrangement of means for transfer of the nucleic acid extraction vessel to a centrifuge.

Unexamined Japanese Patent Publication No. 187077/1992 discloses an automatic pretreatment system for DNA sequencing which comprises a filter unit attached to an aspiration-discharge system, a thermostat and a means for carrying out the necessary mixing and concentration. Unexamined Japanese Patent Publication No. 47278/1997 discloses an extraction apparatus employing a filter system equipped with a vacuum pump in lieu of a centrifuge.

The nucleic acid extraction procedure generally comprises a series of steps, namely hemolysis, leukocyte concentration, cell membrane lysis, and nucleic acid purification. The operations performed in the above-mentioned extraction methods in common are illustrated in the block diagram of FIG. 1. Thus, the nucleic acid extraction procedure generally comprises an operation for charging the vessels with samples and other solutions, a mixing operation necessary for carrying out the reaction, a solid-liquid separating operation, and an operation for removal of unwanted components or recovery of the nucleic acid.

Meanwhile, the conventional nucleic acid extraction apparatus described above is such that the solid-liquid separation in the above series of operations is performed either by means of a centrifuge or by filtration. Therefore, in order that a fully automatic extraction apparatus may be implemented, a centrifuge or a vacuum pump and the associated hardware must be built into the apparatus, with the result that the whole apparatus is inevitably bulky, complicated in construction, and increased in fabrication cost.

As the result of recent advances in the nucleic acid amplification technology, it has become possible to analyze and detect the desired domain of a nucleic acid using a very small amount of sample. Therefore, the technology for extracting nucleic acids from small biological samples with high reliability is more important than the technology for extracting nucleic acids on a large scale.

In clinical examination or diagnosis, a large number of samples must be dealt with at one time. Therefore, it is common practice to perform a nucleic acid extraction using a multiplicity of vessels arranged for respective samples within the limited space of an automated apparatus.

In this case, however, when the above-mentioned so-called open-system microtubes are used as the vessels and the distribution or discharging of the samples, extraction reagents, etc. is carried out, the contamination problem which is most abhorred in clinical diagnosis is liable to take place because of carryovers from one microtube to another.

SUMMARY OF THE INVENTION

The present invention has for its primary object to provide an automatic extraction apparatus by which the extraction of nucleic acid involving a complicated series of operations can be automatically performed.

It is a further object of the invention to overcome the drawbacks of the conventional nucleic acid extraction apparatuses, namely the increased equipment size, complexity and high cost due to the use of a centrifuge or a vacuum pump and the above-mentioned contamination problem and thereby provide a nucleic acid extraction apparatus free from such disadvantages and suited for use in clinical diagnosis.

It is a still further object of the invention to provide an extraction vessel suited for use in the nucleic acid extraction method utilizing a nucleic acid-binding magnetic carrier as described in Unexamined Japanese Patent Publication No. 19292/1997, for instance, and a nucleic acid extraction apparatus tailored to the structural features of said extraction vessel.

The present invention, thus, is directed to the following nucleic acid extraction apparatuses 1–6.

1. A nucleic acid extraction apparatus comprising
(1) a group of extraction vessels each comprising a reactor tube in which a sample, a reagent solution and a magnetic carrier are admixed and reacted, a drain cup for pooling an unwanted component solution and a nucleic acid recovery tube, all as secured to a supporting plate, (2) a distribution means for dispensing a sample or other solution into each of said extraction vessels, (3) a stirring means for stirring the sample solution and magnetic carrier within the extraction vessel, (4) a holding means for holding said magnetic carrier stationary in a position within the extraction vessel, (5) a discharging means for discharging the sample solution from the extraction vessel while said magnetic carrier is held stationary, (6) a heating means for heating the sample solution containing the magnetic carrier in said extraction vessel, and (7) a transfer means for transferring said extraction vessel to the required positions where said distribution means, stirring means, holding means, discharging means, and heating means are respectively disposed.

2. A nucleic acid extraction apparatus comprising (1) a vessel stand adapted to support a group of extraction vessels each comprising a reactor tube to be filled with a magnetic carrier, a sample and a reagent solution, a drain cup and a nucleic acid recovery tube, all as secured to a supporting plate;

(2) a distribution means for dispensing a sample or other solution into the reactor tube of said extraction vessel installed on said vessel stand;

(3) a stirring means for stirring the magnetic carrier, sample, and reagent solution within the reactor tube;

(4) a holding means for holding the magnetic carrier stationary within the reactor tube;

(5) a discharging means for discharging the solution in the reactor tube into the drain cup or nucleic acid recovery tube while the magnetic carrier is held stationary within the reactor tube;

(6) a heating means for heating the reactor tube containing at least said magnetic carrier;

(7) a transfer means for transferring the vessel stand carrying the extraction vessels horizontally; and (8) a control means for controlling said respective means.

3. A nucleic acid extraction apparatus as defined in 2 wherein the control means has a function to control the transfer means in such a manner the vessel stand may be transferred to any of the positions where said distribution means, stirring means, holding means, discharging means, and heating means are respectively disposed.

4. A nucleic acid extraction apparatus as defined in 2 further comprising a means for transferring the extraction vessels and installing them in an array on the vessel stand.

5. A nucleic acid extraction apparatus as defined in 2 wherein the extraction vessel for installing in the vessel stand comprising a reactor tube, a drain cup, and a nucleic acid recovery tube as secured to a supporting plate, a channel cover adapted to provide a connecting path between the nucleic acid recovery tube and the reactor tube as mounted in a top opening of said recovery tube, a cover with a hole for connection of an exhaust nozzle as mounted air-tight in a top opening of said drain cup, a rotary element comprising a piercing pipe for insertion and connection of a distribution nozzle, a valve passageway adapted to provide a connecting path between the reactor tube and the drain cup or the recovery tube, and a rotating grip as mounted air-tight and axial-rotably in a top opening of said reactor tube, and one end of said valve passageway being connected liquid-tight to a discharging pipe extending axially within the reactor tube and the other end being connected air-tight to a passageway communicating with the interior of the drain cup.

6. A nucleic acid extraction apparatus as defined in 5 wherein at least the nucleic acid recovery tube of the extraction vessel is detachable from the reactor tube and drain cup.

The present invention is further directed to the following nucleic acid extraction vessels 7 and 8.

7. A vessel for nucleic acid extraction which comprises a reactor tube, a drain cup, and a nucleic acid recovery tube as secured to a supporting plate, a channel cover adapted to provide a connecting path between the nucleic acid recovery tube and the reactor tube as mounted in a top opening of said recovery tube, a cover with a hole for connection of an exhaust nozzle as mounted air-tight in a top opening of said drain cup, a rotary element comprising a piercing pipe for insertion and connection of a distribution nozzle, a valve passageway adapted to provide a connecting path between the reactor tube and the drain cup or the recovery tube, and a rotating grip as mounted air-tight and axial-rotably in a top opening of said reactor tube, and one end of said valve passageway being connected liquid-tight to a discharging pipe extending axially within the reactor tube and the other end being connected air-tight to a passageway communicating with the interior of the drain cup.

8. A nucleic acid extraction vessel as defined above wherein at least said nucleic acid recovery tube is detachable from said reactor tube and drain cup.

Furthermore, the present invention provides the following nucleic acid extraction methods 9–12.

9. A method for nucleic acid extraction using the nucleic acid extraction apparatus of the invention which comprises (a) a step of extracting a nucleic acid from a sample and causing it to be adsorbed on a magnetic carrier in a reactor tube of an extraction vessel;

(b) a step of separating the magnetic carrier carrying the nucleic acid adsorbed thereon from the solution;

(c) a step of washing the separated magnetic carrier;

(d) a step of eluting the nucleic acid from the magnetic carrier, and (e) a step of recovering the nucleic acid.

10. A method for nucleic acid extraction as defined above wherein said (a) extraction step, (c) washing step, and (d) elution step are carried out by introducing an extraction solution, a wash solution, and an eluent, respectively, into the reactor tube containing the magnetic carrier by using the distribution means and then stirring the mixture by using the stirring means.

11. A method for nucleic acid extraction as defined above wherein said (b) magnetic carrier separation step and (e) nucleic acid recovery step comprise discharging the solution from the reactor tube into the drain cup and nucleic acid recovery tube, respectively, by using the discharging means while the magnetic carrier is retained stationary within the reactor tube by using the holding means.

12. A method for nucleic acid extraction as defined above wherein said (d) nucleic acid elution step comprises drying the magnetic carrier carrying the nucleic acid adsorbed thereon by using the heating means, introducing an eluent into the reactor tube containing said magnetic carrier by using the distribution means, stirring the magnetic carrier in the eluent by using the stirring means, heating the solution by using the heating means, and stirring it by using the stirring means again.

BRIEF DESCRIPTION OF THE DRAWINGS

FIG. 5 is a view showing a nucleic acid extraction apparatus embodying the principles of the invention, wherein

DETAILED DESCRIPTION OF PREFERRED EMBODIMENTS

Figure 1:
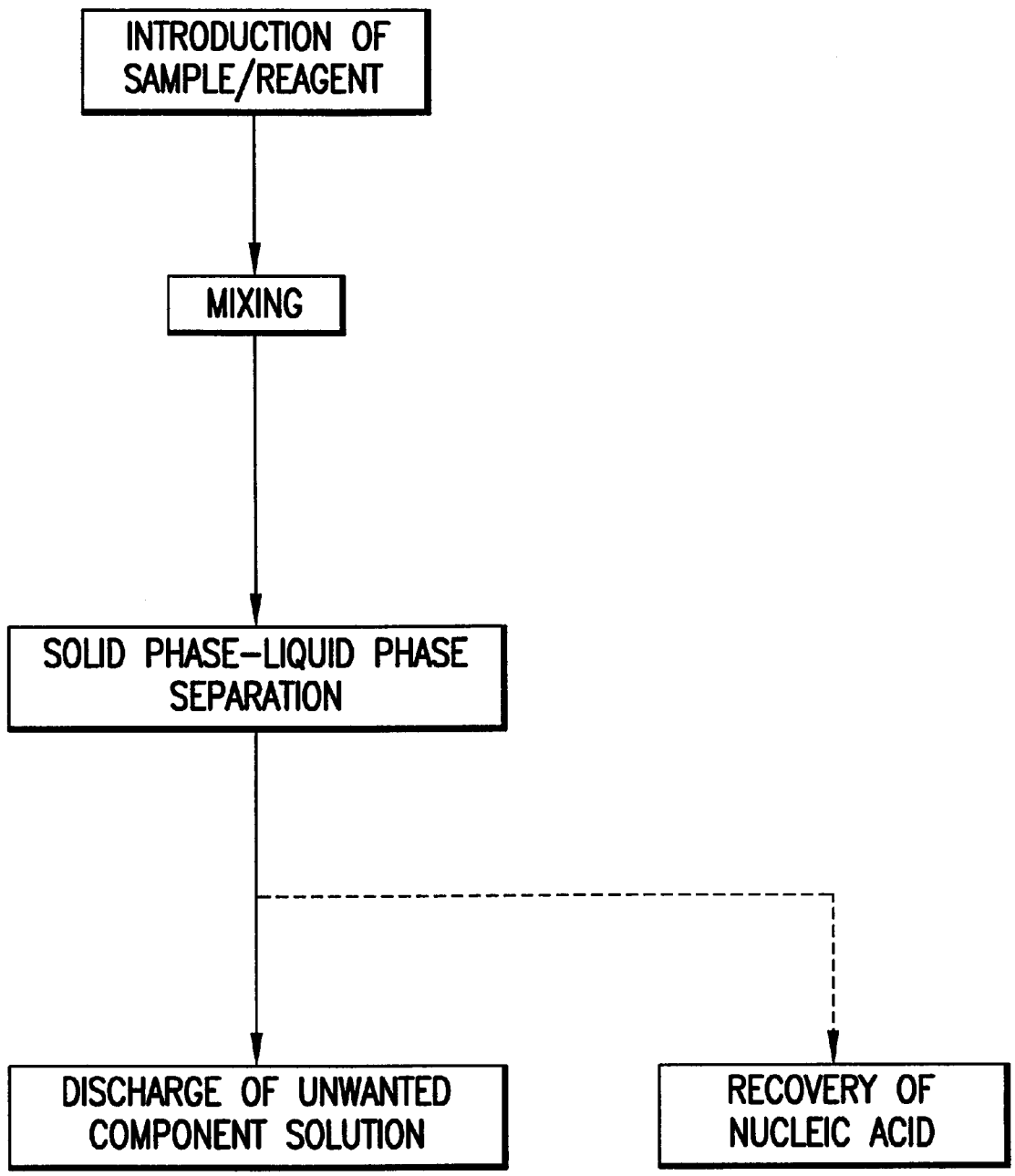
FIG. 1 is a block diagram showing operations common to a general procedure for nucleic acid extraction.

The present invention relates to a nucleic acid extraction apparatus including a group of nucleic acid extraction vessels each comprising a reactor tube, a rain cup for pooling an unwanted component solution, and nucleic acid recovery tube as a unit, which is adapted to prevent vessel-to-vessel carryover in the extraction procedure and hence eliminate the risk for contamination. In this specification, the above vessel is referred to as "nucleic acid extraction vessel" or sometimes briefly as "extraction vessel".

Of the above extraction vessel, the reactor tube is a component unit in which the reaction necessary for treatment of a sample or analysis thereof for an objective component is carried out, the drain cup is a component unit in which the unwanted component solution formed by the reaction for said treatment or analysis is pooled, and the recovery tube is a component unit in which the objective nucleic acid is recovered.

Furthermore, in this extraction vessel, the reactor tube, drain cup and recovery tube are fixed in tandem to a supporting plate.

The sample which can be dealt with includes but is not limited to biological materials from human or animal, such as the blood, serum, buffy coat, urine, feces, seminal solution, saliva, hair, sputum, and tissue cells (inclusive of cultured cells), as well as various other cells and cell cultures. Among them, preferred are biological materials from human.

This invention is now described in detail, reference being had to the accompanying drawings. The reference numerals used in the following description correspond to the numerals used in the drawings.

1. Extraction Vessel

Figure 2:
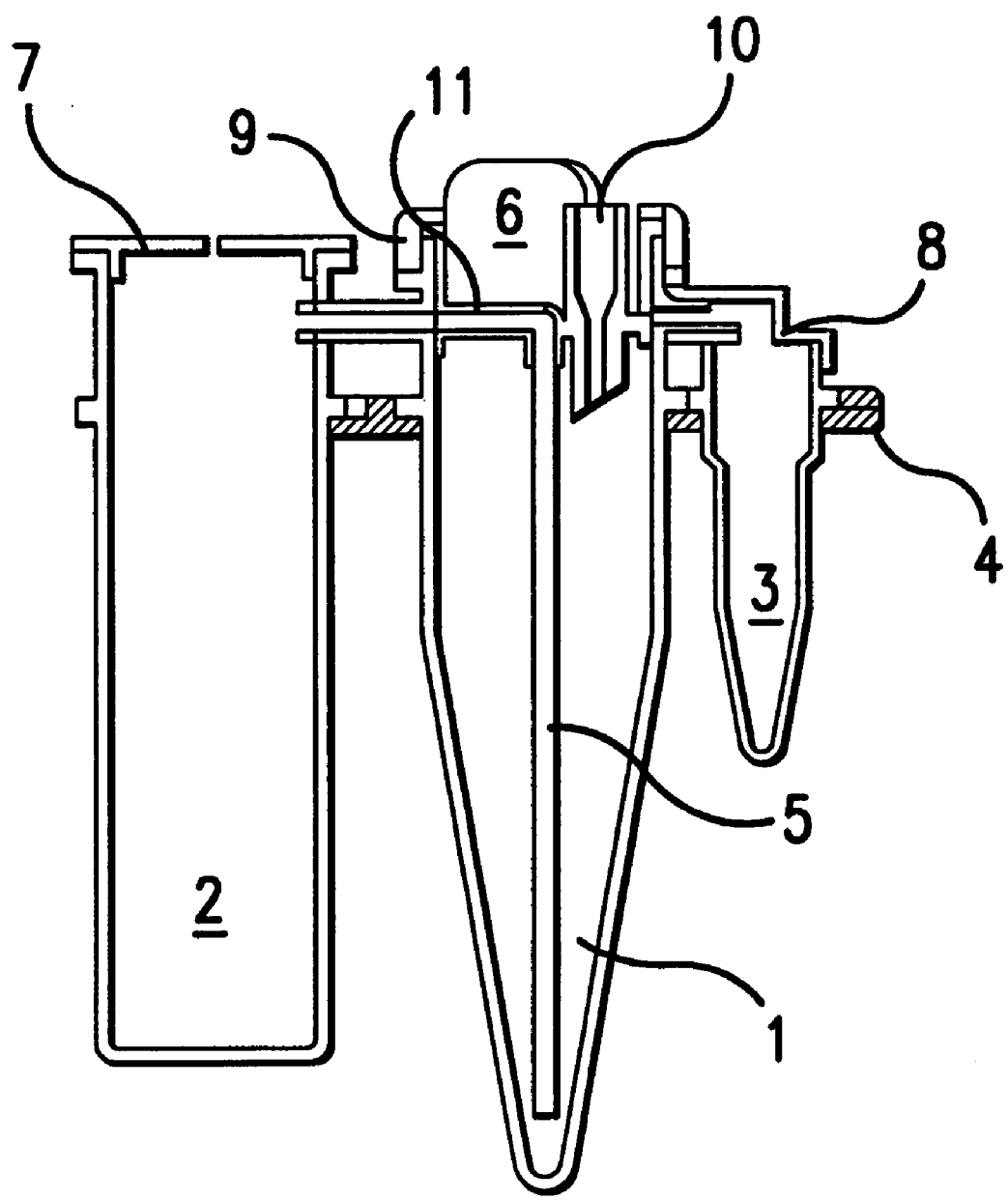
FIG. 2 is a sectional view showing a nucleic acid extraction vessel for use in the invention, wherein the reference numeral 1 represents a reactor tube, 2 a drain cup, 3 a recovery tube, 4 a supporting plate, 5 a discharging pipe, 6 a rotary element (valve), 7 a cover, 8 a channel cover, 9 a retaining cover, 10 a piercing pipe, and 11 a valve passageway.

FIG. 2 is a sectional side elevation view showing a typical extraction vessel for use in the nucleic acid extraction apparatus of the invention.

The extraction vessel essentially comprises a reactor tube 1 in which a sample is mixed and reacted with reagents etc., a drain cup 2 for pooling an unwanted component solution and a tube 3 for recovering the nucleic acid extracted from the sample, and those component units are fixed tandem to a supporting plate 4. It should be understood that this fixation may optionally be a disconnectable one.

Of this extraction vessel, said three component units, namely the reactor tube, drain cup, and recovery tube, may be molded integrally or in such a manner that at least one of the component units may be disconnected from the other units. It is preferably arranged so that at least the nucleic acid recovery tube 3 may be detached from the other units, and even from the supporting plate 4, for example after completion of nucleic acid extraction.

The drain cup 2 has a cover 7, the recovery tube 3 has a channel cover 8, and the reactor tube 1 has a rotary element 6 (a valve), on the top openings thereof. The rotary element 6 is secured to the reactor tube 1 through a retaining cover 9 in such a manner that it may be rotated about the axis of the reactor tube 1. As installed within the reactor tube 1, a discharging pipe 5 extending in the axial direction of the reactor tube is connected liquid-tight to a valve passageway 11 in said rotary element 6. Preferably, the lower end of the discharging pipe 5 and the inner bottom of the reactor tube 1 are spaced apart by about 1–10 mm.

Figure 3A:
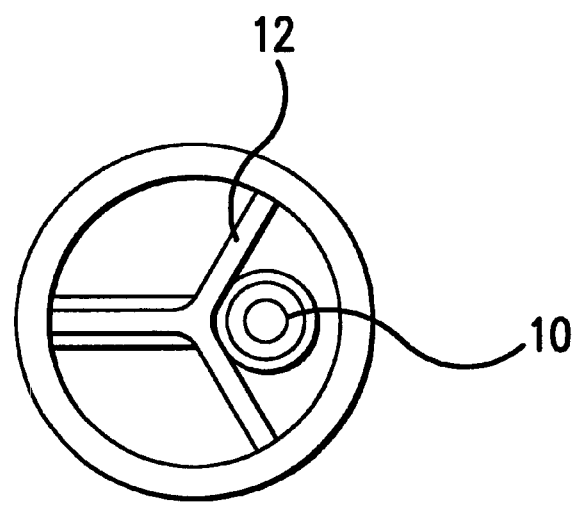
FIGS. 3a and 3b are schematic views showing the rotary element (valve) 6 of the nucleic acid extraction vessel, wherein the reference numeral 10 and 11 indicate the same piercing pipe and valve passageway as shown in FIG. 2 and the numeral 12 represents a grip (ribs).
Figure 3B:
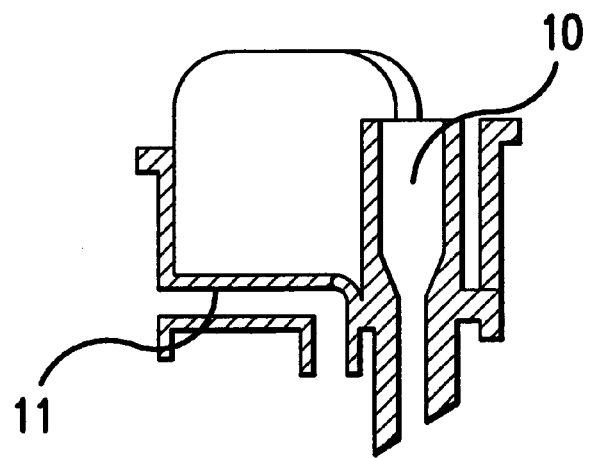

FIG. 3 shows the rotary element 6. FIG. 3a is a top view of the rotary element and FIG. 3b is a side elevation view thereof. The rotary element 6 is connected air-tight to the top of the reactor tube 1 and provides various passageways. The rotary element 6 comprises a piercing pipe 10, a valve passageway 11, and an operating grip (ribs) 12 which are integrally formed.

Figure 4:
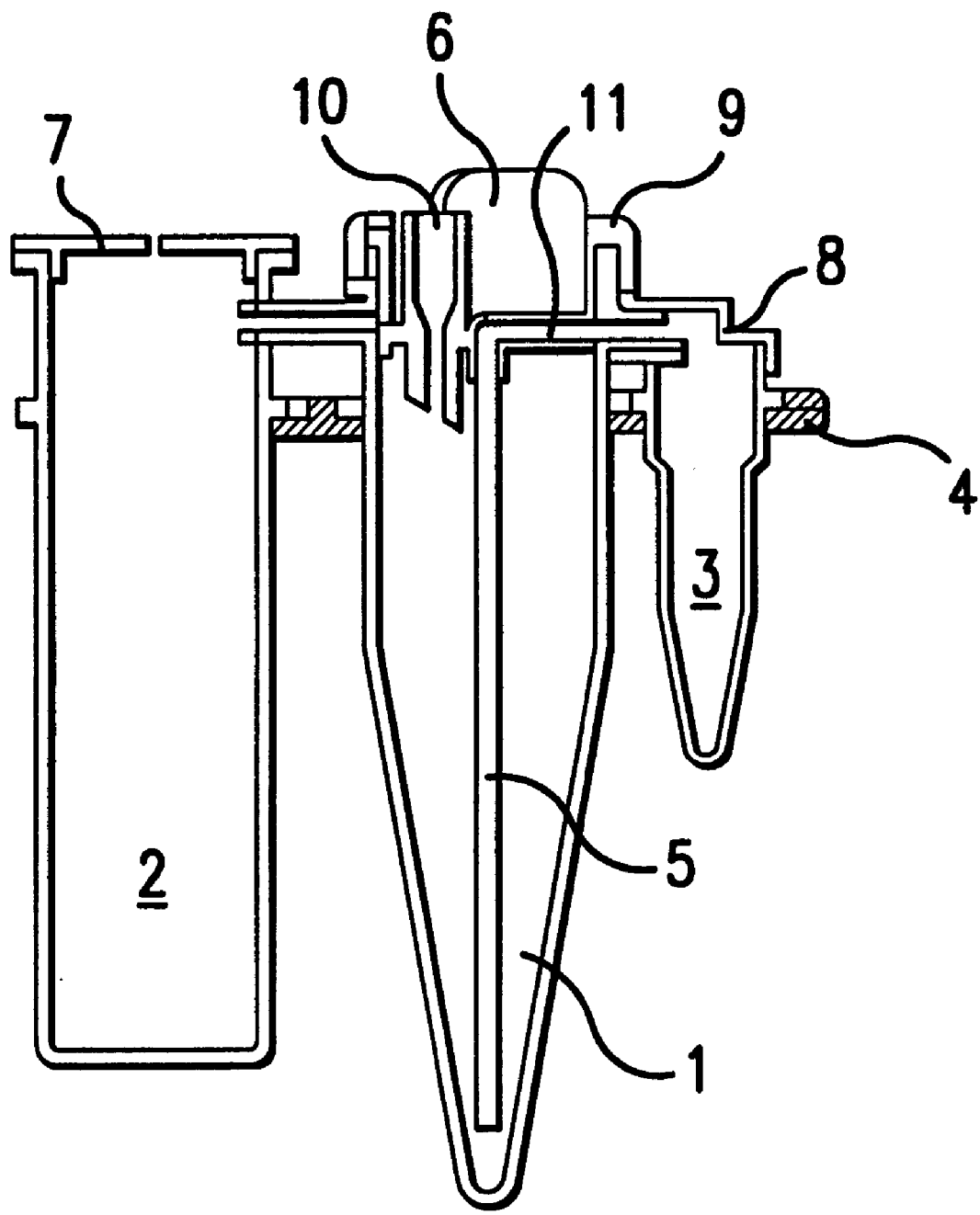
FIG. 4 is a sectional view showing a nucleic acid extraction vessel, wherein the element 6 has been axially rotated through 180 degrees from the position shown in FIG. 2. Each reference numeral represents the same as shown in FIG. 2.

The piercing pipe 10 is used for charging the reactor tube 1 with a sample and a reagent solution and feeding pressurized air for applying a pressure to the interior of the reactor tube 1. Preferably this piercing pipe 10 is tapered, i.e. progressively reduced in inner diameter, toward the reactor tube 1. The valve passageway 11 has one end connectable liquid-tight to the discharging pipe 5 in the axial direction of the reactor tube 1 and the other end adapted for liquid-tight connection to a flow passageway communicating with the interior of the drain cup 2, thus forming a drain passageway for discharging the reaction mixture from the reactor tube 1 to the drain cup 2. The rotary element 6 is so constructed that as the grip 12 is rotated, the element 6 is rotated about the axis of the reactor tube 1. Assuming, by way of illustration, that the rotary element 6 is in the position shown in FIG. 2, the reaction mixture solution in the reactor tube 1 can be allowed to drain into the drain cup 2 through the drain passageway extending from the reactor tube 1 through the discharging pipe 5 and valve passageway 11 to the drain cup 2. As the rotary element 6 is rotated through 180 degrees about the axis of the reactor tube 1 from the above position, the flow passageway consisting of the discharging pipe 5 and valve passageway 11 is brought into communication with the recovery tube 3 through a flow passageway formed by the channel cover 8, as illustrated in FIG. 4, so that the reaction product in the reactor tube 1 can be withdrawn into the recovery tube 3.

In this manner, the channel cover 8 not only covers the top opening of the recovery tube 3 but also provides at least a part of the flow passageway for discharging the objective nucleic acid from the reactor tube 1 into the recovery tube 3.

The cover 7 disposed across the top opening of the drain cup 2 is preferably provided with a hole therein so that an exhaust nozzle may be connected thereto when the reaction mixture is to be discharged from the reactor tube 1 into the drain cup 2.

The extraction vessel may be molded from virtually any material and such conventional materials as glass, polypropylene, polyvinyl chloride, and silicone-coated general resin, among others, can be employed. Among those materials, polypropylene is particularly preferred because the objective nucleic acid will not be adsorbed thereon.

The geometry of the extraction vessel is not particularly restricted. For example, the reactor tube 1 may be a conical one, the drain cup 2 may be cylindrical, and the recovery tube 3 may be shaped like an ordinary microtube, for example a tube having a conical bottom.

2. Nucleic Acid Extraction Apparatus

The construction of the nucleic acid extraction apparatus of the invention is now described.

Figure 5A:
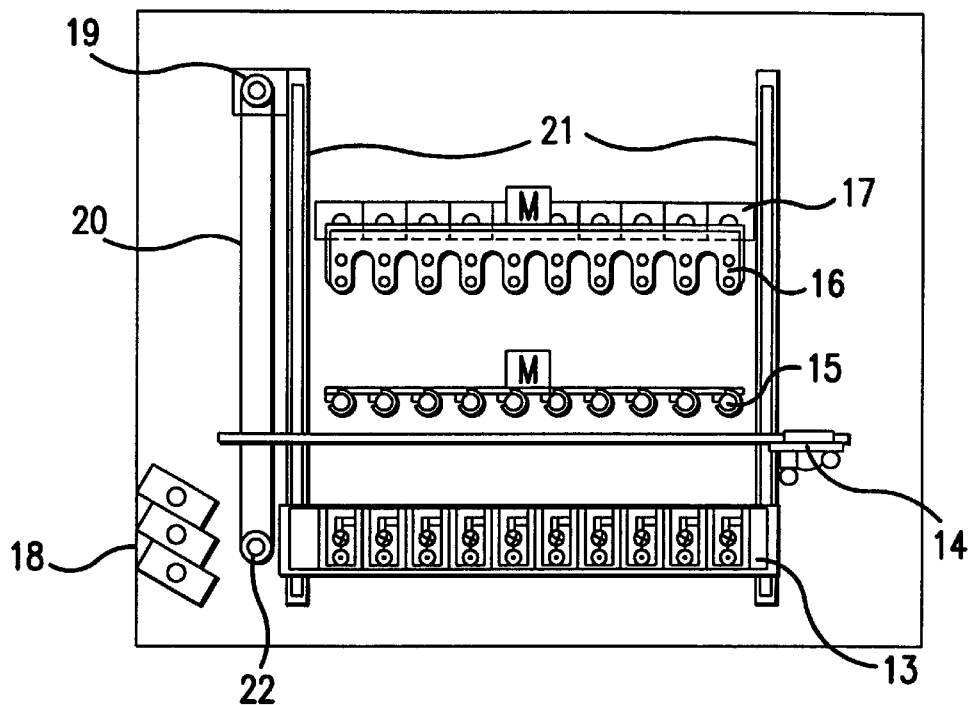
FIG. 5a is a top view and FIG. 5b is a side view. In the views, the reference numeral 13 represents a vessel stand, 14 a distribution means, 15 a stirring means, 16 a discharging means, 17 a holding/heating means, 18 a reagent bottle or bottle group, 19 a motor, 20 a continuous belt, and 21 a rail.
Figure 5B:
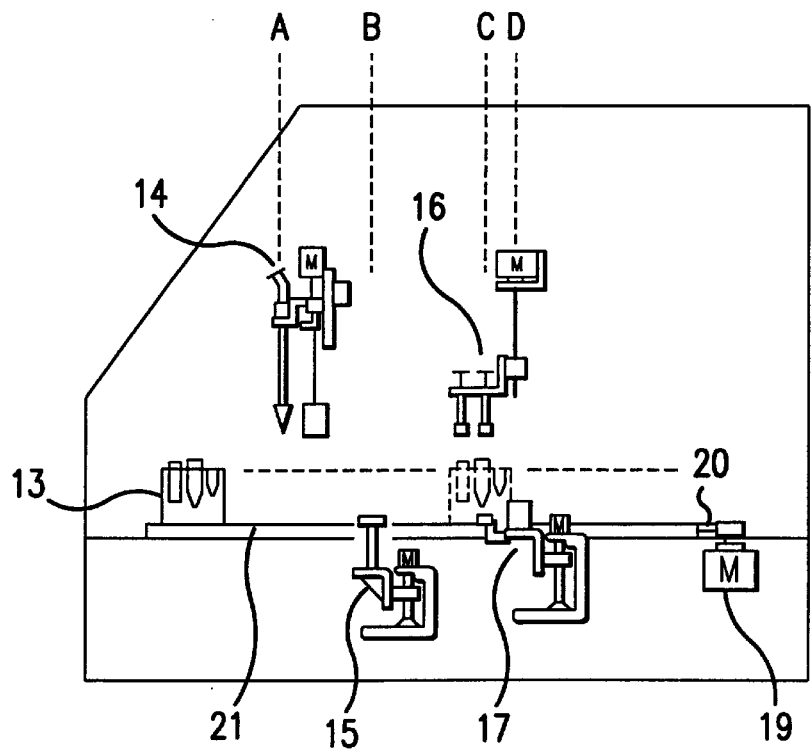

FIG. 5a and FIG. 5b are a top view and a side view, respectively, of a nucleic acid extraction apparatus embodying the principles of the invention. In those views, the reference numeral 13 represents a vessel stand on which said group of extraction vessels is mounted, 14 a distribution means having a distribution nozzle for dispensing the sample and reagent solutions into the reactor tube of said extraction vessel and a rotary arm for rotating said rotary element 6. The reference numeral 15 represents a stirring means for admixing the solutions in the reactor tube 1 of said extraction vessel, 16 represents a discharging means for withdrawing the solution in said reactor tube 1 into said drain cup 2 or said recovery tube 3, and 17 represents an integral unit comprising a holding means for holding a magnetic carrier stationary on the internal wall (internal bottom area) of the reactor tube 1 and a heating means for heating the solution in the reactor tube 1, which works in contacting with the external wall (external bottom area) of the reactor tube 1.

The reference numeral 18 represents a reagent bottle or bottle group containing the reagents (extraction solvent, wash solution, eluent, etc.) for use in the nucleic acid extraction procedure.

The reference numerals 19, 20, 21 and 22 taken together represent a means for transfer of the vessel stand 13. Thus, the numeral 19 represents a motor, 20 a continuous belt, 21 a rail, and 22 a pulley. Thus, the vessel stand 13 carrying the extraction vessel traverses along the rails 21 as the motor 19 and, hence, the belt 20, and pulley 22 are driven, and as shown in FIG. 5b, successively occupies the positions A, B, C, and D where said distribution means 14, stirring means 15, holding means 17a and discharging means 16, and heating means 17b are respectively disposed. In this specification, those means are collectively referred to as a transfer means.

The apparatus of the invention may further include a means for transferring extraction vessels to the vessel stand and disposing them thereon.

The detailed structure of the means represented by the reference numerals 14–17 are now described.

Figure 6:
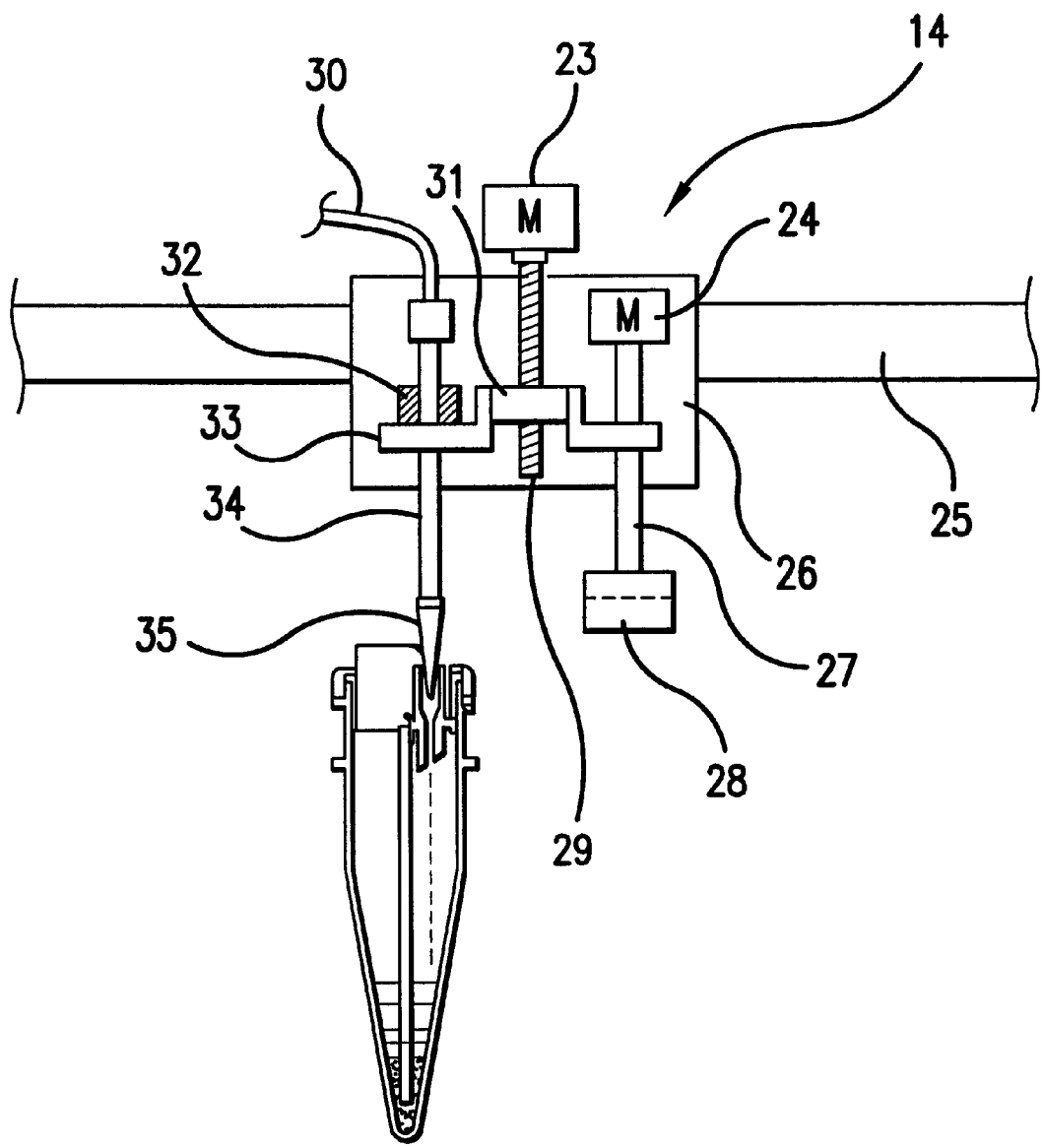
FIG. 6 is a schematic view showing a typical distribution means 14 for use in the invention, wherein the reference numerals 23 and 24 each represents a motor and the reference numeral 25 represents a rail, 26 a linear motor base, 27 a rotary arm, 28 a rotary arm grip, 29 a pole screw, 30 a tube, 31 a movable piece, 32 a spring, 33 an L-shaped metal, 34 a distribution nozzle, and 35 a pad.

FIG. 6 is a schematic diagram illustrating the distribution means 14 for dispensing solutions into the reactor tube 1 of the extraction vessel. The mechanical components of this distribution means 14 are mounted on a liner motor base 26 so that they may traverse along rails 25 horizontally. Connected to the motor 23 is a pole screw 29, whereby a movable piece 31 is caused to move up and down in response to rotation of the pole screw. This movable piece 31 is symmetrically flanked by a pair of L-shaped metals 33 and the distribution nozzle 34 is attached to one of them, while the rotary arm 27 is attached to the other L-shaped metal.

Fitted to the forward end of the distribution nozzle 34 is a resin pad 35 shaped to fit the bore of the piercing pipe 10 of the rotary element 6 so that said forward end may come into connection with the inlet to the reactor tube 1, that is to say the piercing pipe 10 of the rotary element 6. The reference numeral 32 represents a spring and the reference numeral 30 represents a tube for feeding the reagent and other solutions from the reagent bottle or bottle group 18, said tube 20 being connected to the distribution nozzle 34 in a liquid-tight manner. The rotary arm 27 attached to the L-shaped metal 33 on the opposite side to the distribution nozzle 34 is adapted to rotate the rotary element C. This arm 27 has a rotary arm grip 28 shaped to fit the grip 12 of the rotary element 6 at its forward end and is driven by a motor 24.

Figure 7:
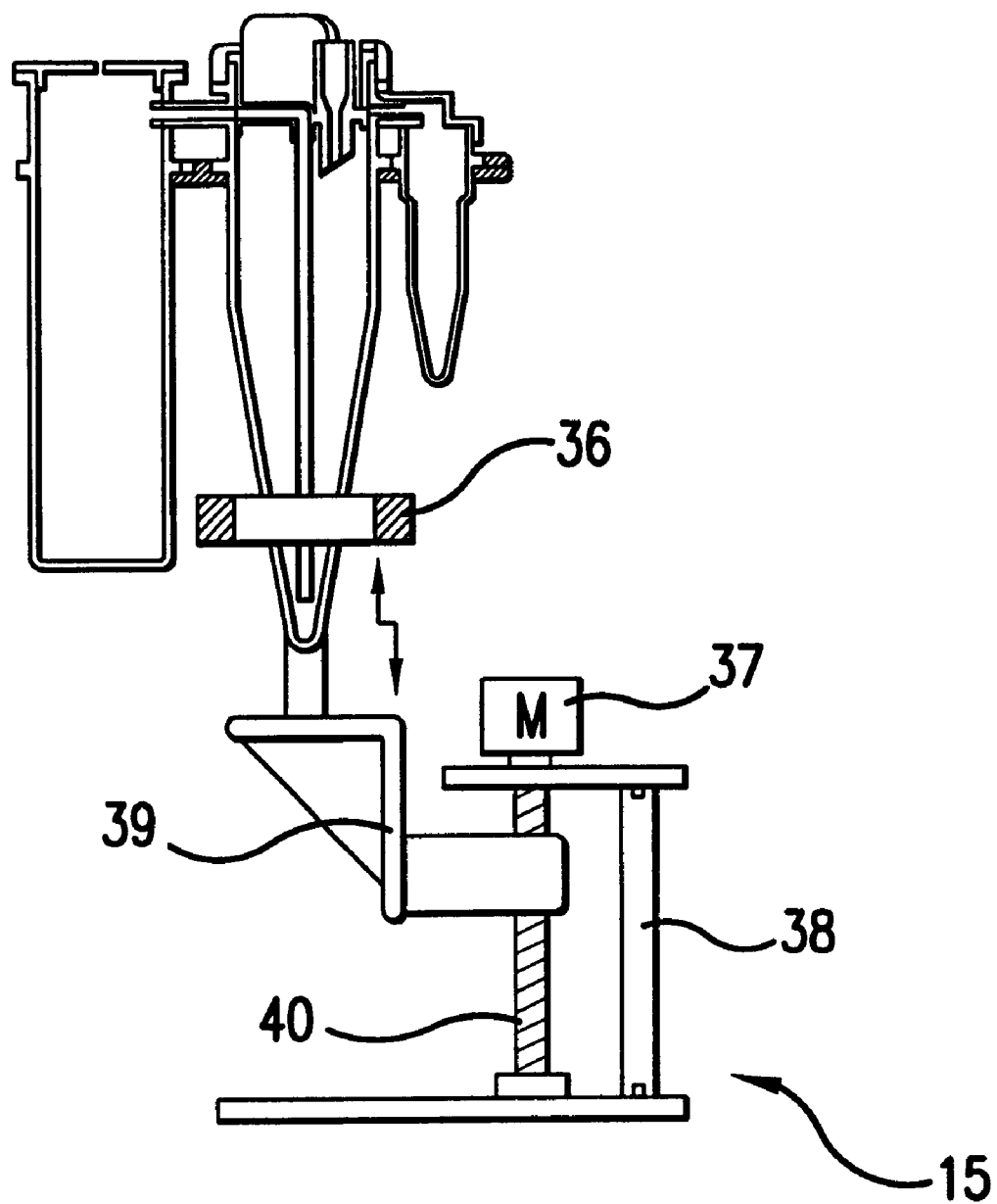
FIG. 7 is a schematic view showing a typical stirring means 15 for use in the invention, wherein the reference numeral 36 represents a ring magnet, 37 a motor, 38 and 39 each a fixing metal, and 40 a pole screw.

FIG. 7 is a schematic view showing the stirring means 15 for stirring the solution within the reactor tube 1 of the extraction vessel. The stirring is effected as a ring-shaped permanent magnet (ring magnet) 36 reciprocates vertically with the reactor tube 1 being included in its central hole. The reference numeral 37 represents a motor, 40 a pole screw, and 38 and 39 each represents a fixing plate supporting the stirring mechanism. As the fixing plate 39 reciprocates vertically in response to rotation of the pole screw 40, the ring magnet 36 secured to this fixing plate is also caused to reciprocate vertically in synchronism.

Figure 8:
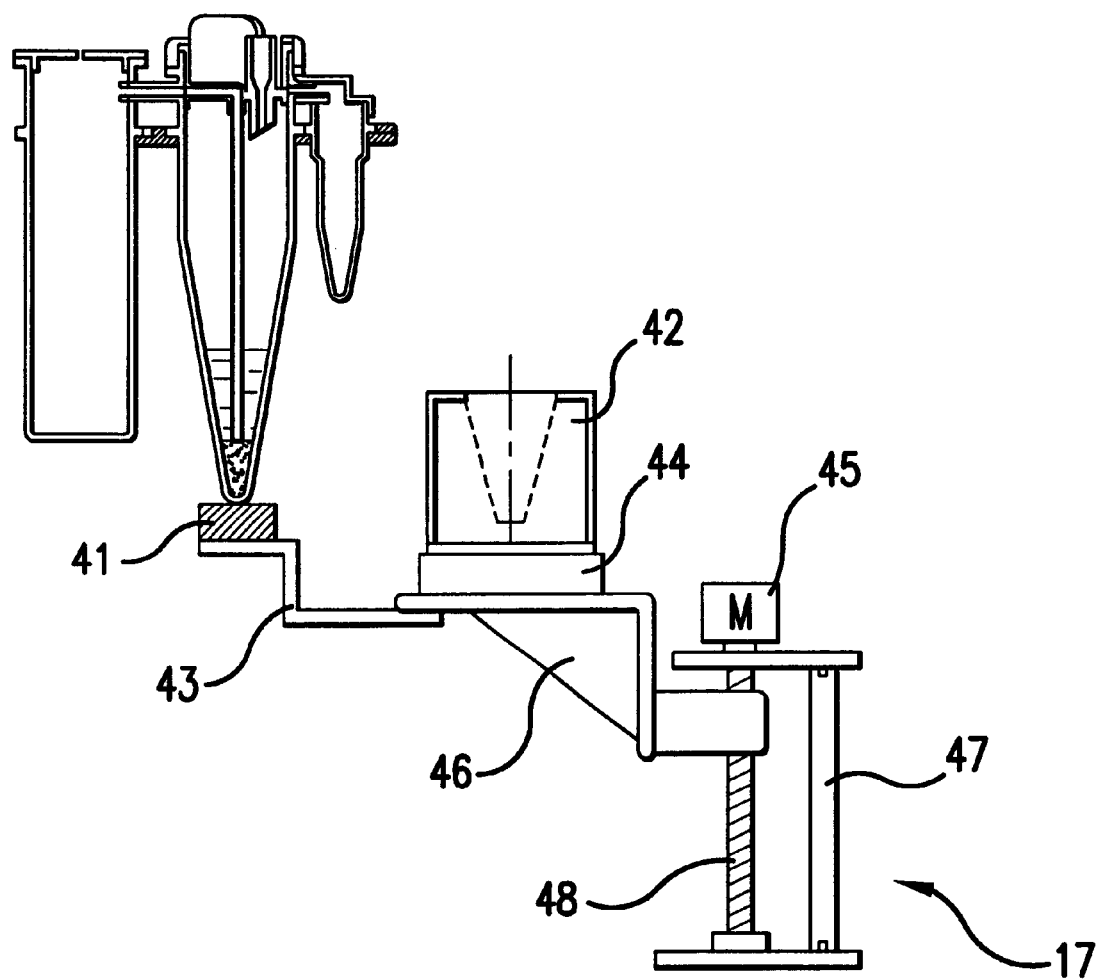
FIG. 8 is a schematic view showing a typical unit 17 comprising a holding means 17a and a heating means 17b for use in the invention, wherein the reference numeral 41 represents a permanent magnet, 42 a heating block, 43 a mounting metal, 44 a platform, 45 a motor, 46 and 47 each a fixing metal, and 48 a pole screw.

FIG. 8 is a schematic diagram showing an integral unit 17 comprising a holding means and a heating means. The holding means 17a is comprised of a permanent magnet 41 by which the magnetic carrier contained in the reactor tube 1 of the extraction vessel is retained on the inside wall (inside bottom wall) of the reactor tube. The heating means 17b comprises a heating block 42 made of a metal such as aluminum and having a recess complementary to a bottom portion of the reactor tube 1 for accepting said bottom portion and a platform 44 having a built-in plane heater (not shown) for controlling the temperature of said heating block. The integral unit 17 includes a motor 45, a pole screw 48, and fixing metals 43, 46 and 47 for vertically reciprocating the permanent magnet 41, heating block 42 and platform 44.

Figure 9:
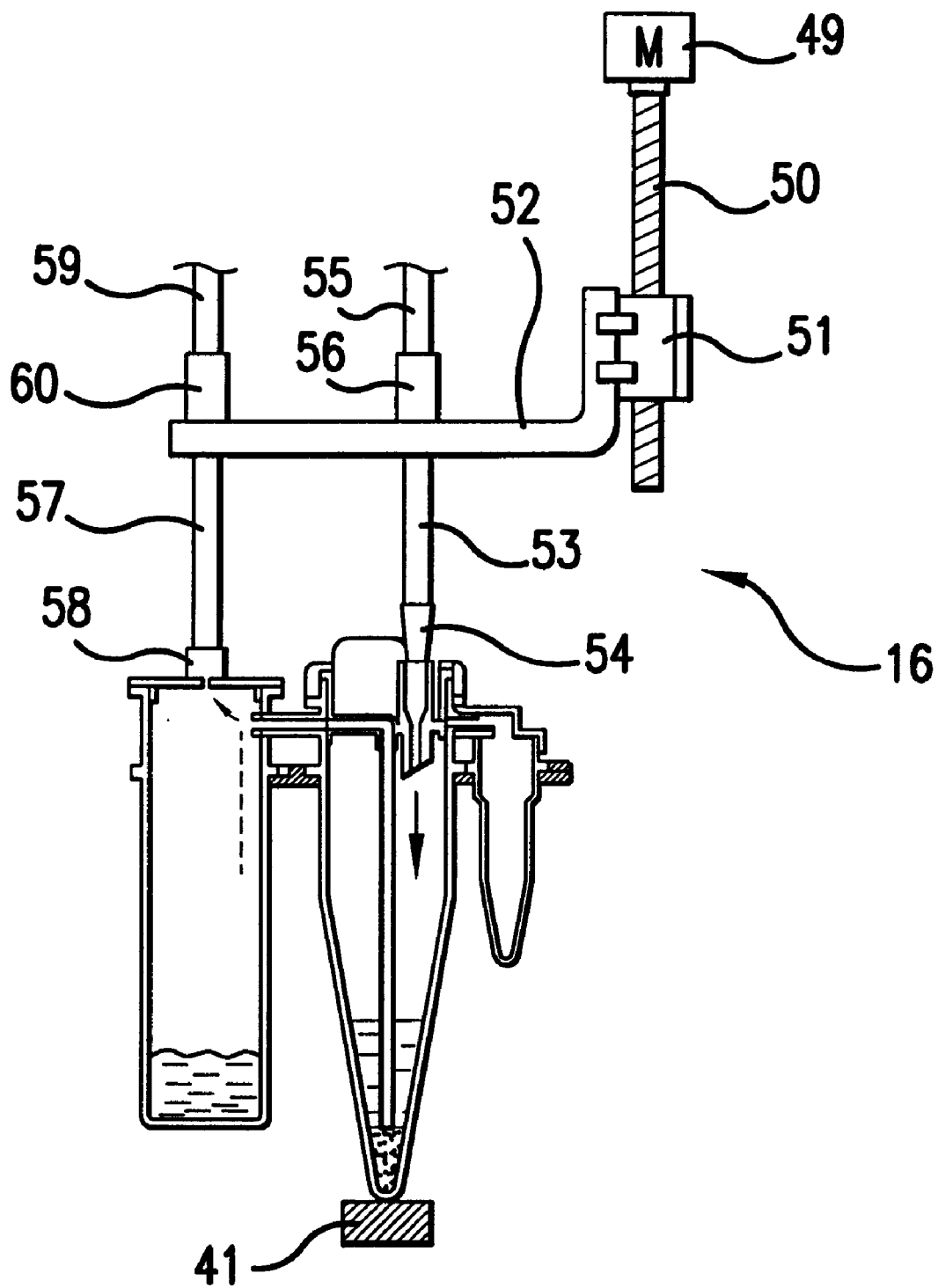
FIG. 9 is a schematic view showing a typical discharging means 16 for use in the invention, wherein the reference numeral 41 represents a permanent magnet, 49 a motor, 50 a pole screw, 51 a movable piece, 52 an L-shaped metal, 53 a pressure nozzle, 54 a pad, 55 a tube, 56 a joint metal, 57 an exhaust nozzle, and 58 a pad.

FIG. 9 is a schematic view showing the discharging means 16 positioned on the extraction vessel. Since this discharging means 16 must also be movable vertically, it comprises a motor 49, a pole screw 50 and a movable piece 51 adapted to move up and down in response to rotation of said pole screw. This discharging means further comprises a pressure nozzle 53 and an exhaust nozzle 57 as attached to an L-shaped metal 52 connected to said movable piece 51. The forward end of the pressure nozzle 53 carries a resin pad 54 complementary to the inside geometry of the inlet to the reactor tube 1 of the extraction vessel, that is to say the piercing pipe 10 of the rotary element 6. This pressure nozzle 53 is connected air-tight to a pressurized air supply tube 55 through a joint metal 56.

On the other hand, the forward end of the exhaust nozzle 57 is fitted with a resin pad 58 conforming to a hole in the cover 7 mounted on the top opening of the drain cup 2. This exhaust nozzle 57 is connected air-tight to a tube 59 for discharging air from the drain cup 2 to a disposal bottle (not shown) through a joint metal 60.

The nucleic acid extraction apparatus of this invention basically comprises said various means (distribution means, stirring means, holding means, discharging means, heating means, and transfer means) and those means are controlled by a computer (not shown).

3. Nucleic Acid Extraction Method

The method of extracting a nucleic acid using the above-described nucleic acid extraction apparatus of the invention is now described. The nucleic acid extraction method using the above apparatus of the invention can be carried out by the technique utilizing a magnetic carrier as described in Unexamined Japanese Patent Publication No. 19292/1997, for instance. The published literature is incorporated herein by reference.

This nucleic acid extraction method comprises feeding magnetic silica beads containing a superparamagnetic metal oxide, a sample containing the objective nucleic acid, and a solvent for nucleic acid extraction into the extraction vessel, mixing them together to let the nucleic acid attached to the magnetic silica beads, applying a magnetic field to the vessel to separate the magnetic silica beads carrying the nucleic acid from the solution (B/F separation), and finally eluting the nucleic acid from the magnetic silica beads.

Figure 10:
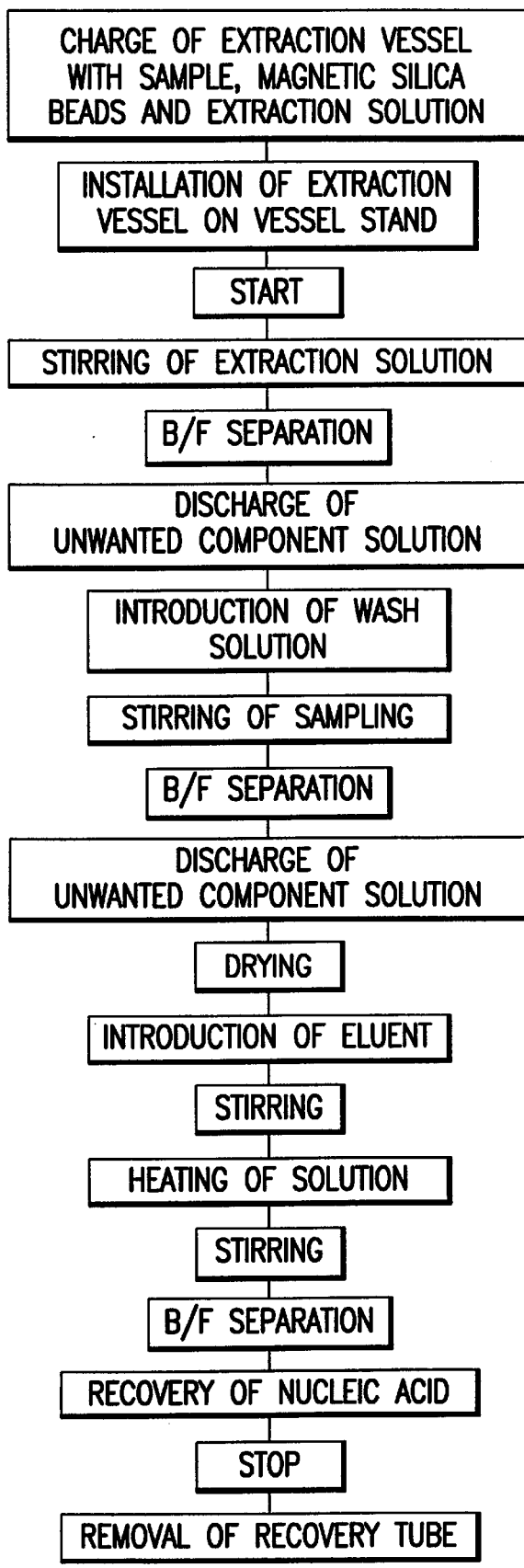
FIG. 10 is a flow-chart showing the nucleic acid extraction procedure using the nucleic acid extraction apparatus of the invention.
Figure 11:
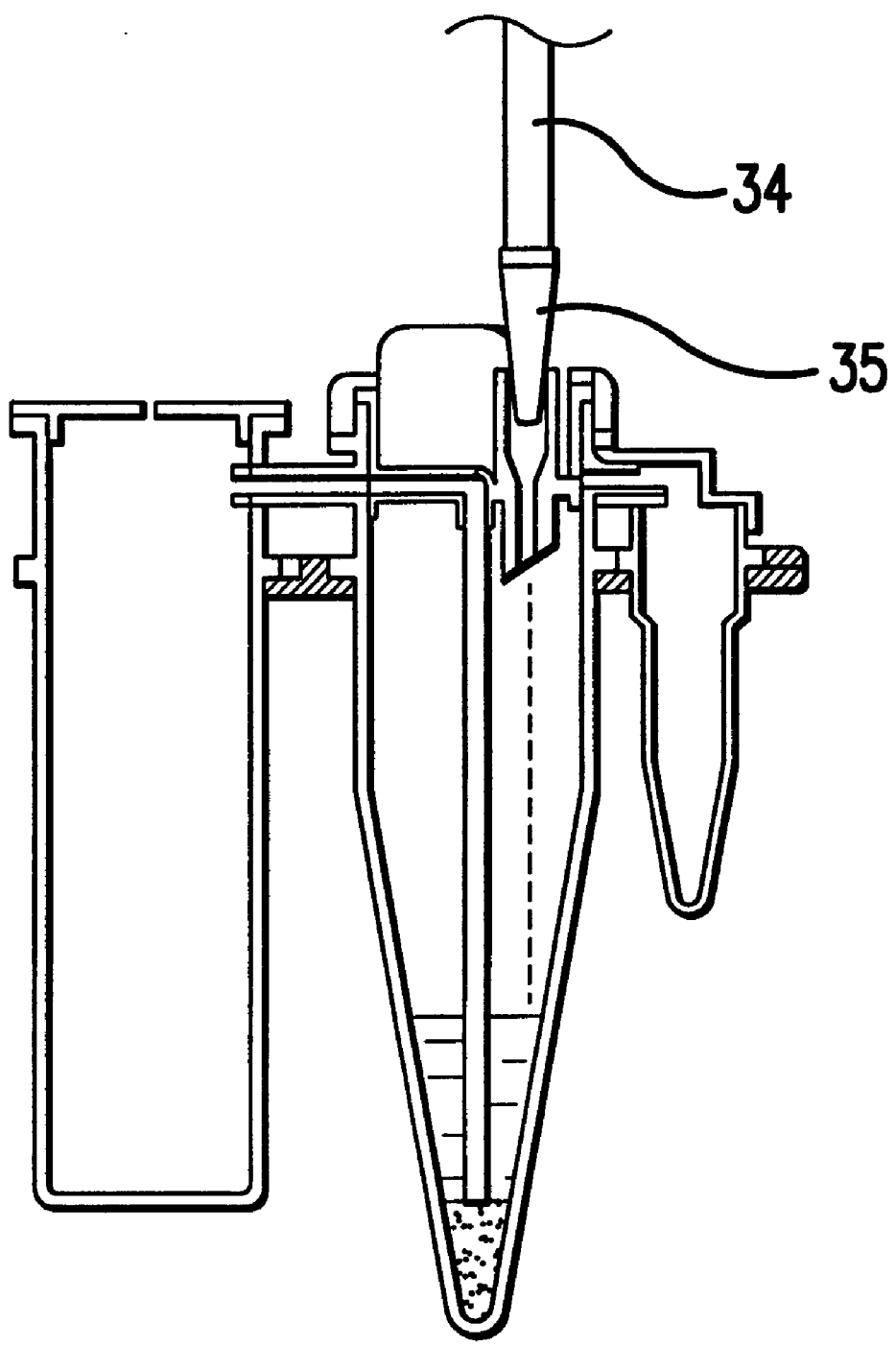
FIG. 11 is a schematic diagram illustrating a distribution step in the nucleic acid extraction procedure using the nucleic acid extraction apparatus of the invention, wherein the reference numeral 34 represents a dispensing nozzle and 35 a pad.

The sequence of steps according to this nucleic acid extraction method (flow-chart) is shown in FIG. 10. The method of using the nucleic acid extraction apparatus of the invention is now described in accordance with this flow-chart. Schematic diagrams pertinent to the respective steps are shown in FIG. 11–16.

First, the reactor tube 1 of the extraction vessel is charged with the sample (for example a biological sample such as blood) and the magnetic silica beads for attraction of nucleic acid. In consideration of safety, this procedure is generally carried out by the operator in a clean bench or the like. During this procedure, the reagent solution for extraction is fed to the reactor tube.

The extraction vessel thus containing the sample, magnetic silica beads, and extraction reagent solution in the reactor tube is transferred and installed on the vessel stand 13 of the nucleic acid extraction apparatus (FIGS. 5a and 5b). This transfer and installation of the extraction vessel on the vessel stand 13 can be carried out utilizing the vessel transfer and installation means with which the extraction apparatus is optionally provided.

The foregoing represents a preparation stage preceding the operation of the apparatus of this invention. After the above installation of the extraction vessel, the nucleic acid extraction procedure is started, for example by pressing a start button (not shown). The first step in this procedure is a stirring step where the solution in the reactor tube 1 is stirred to extract nucleic acid from the sample and cause it to be adsorbed on the magnetic silica beads as described in Unexamined Japanese Patent Publication No. 19292/1997.

Figure 12:
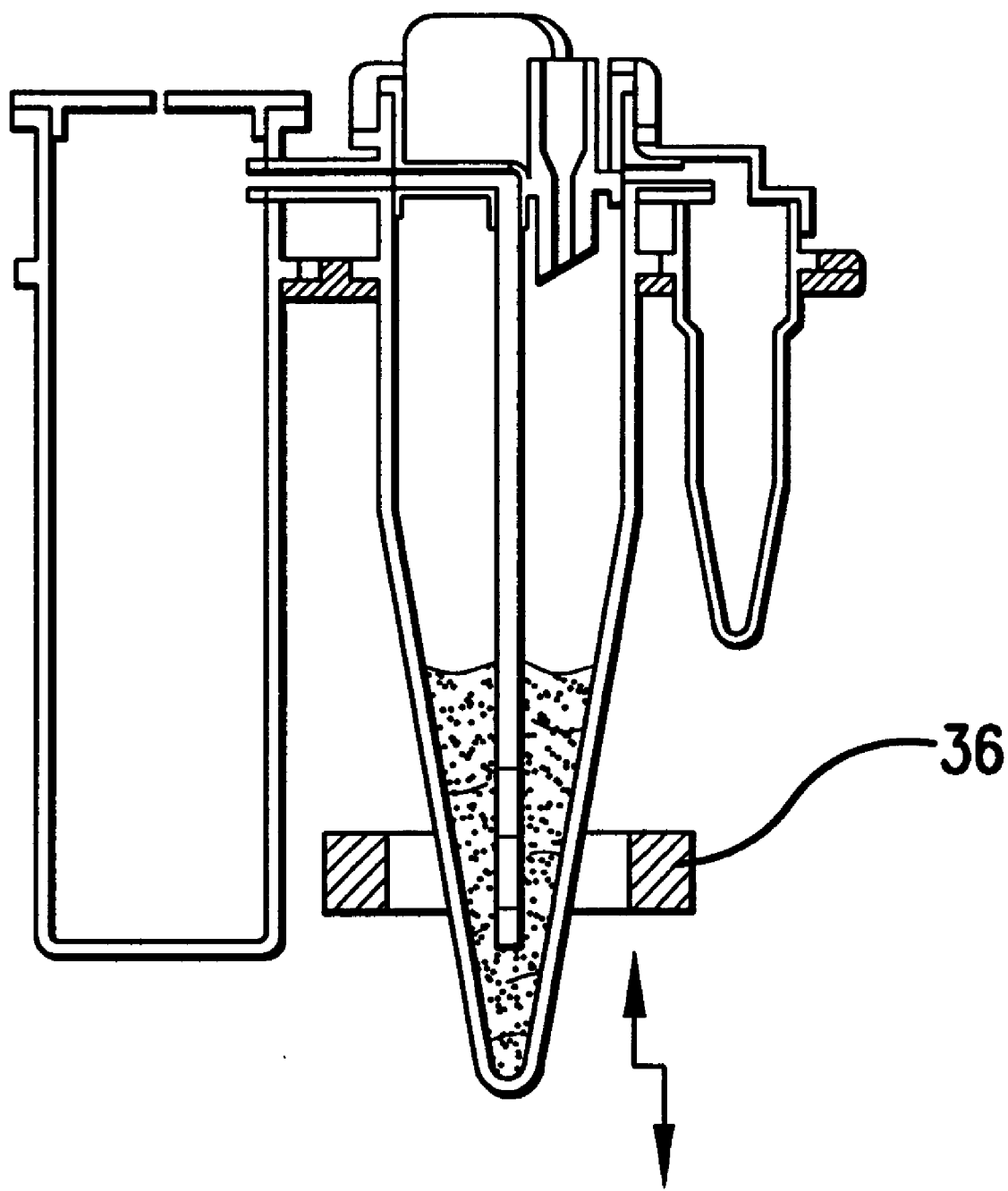
FIG. 12 is a schematic view showing a stirring step in the nucleic acid extraction procedure using the nucleic acid extraction apparatus of the invention, wherein the reference numeral 36 represents a ring magnet.

The vessel stand 13 is transferred, by said transfer means, to position B where the stirring means 15 is located (FIG. 5b). The vessel stand remains stationary in this position during the solution in the reactor tube 1 is stirred for thorough mixing. As shown in FIG. 12, this stirring and mixing is effected as the ring magnet 36 of the stirring means 15 reciprocates vertically with the reactor tube 1 being positioned within its central hole to thereby cause the magnetic silica beads in the reactor tube 1 to move up and down. The stroke of reciprocation of the ring magnet 36 and the stirring time can be judiciously selected as necessary.

Figure 13:
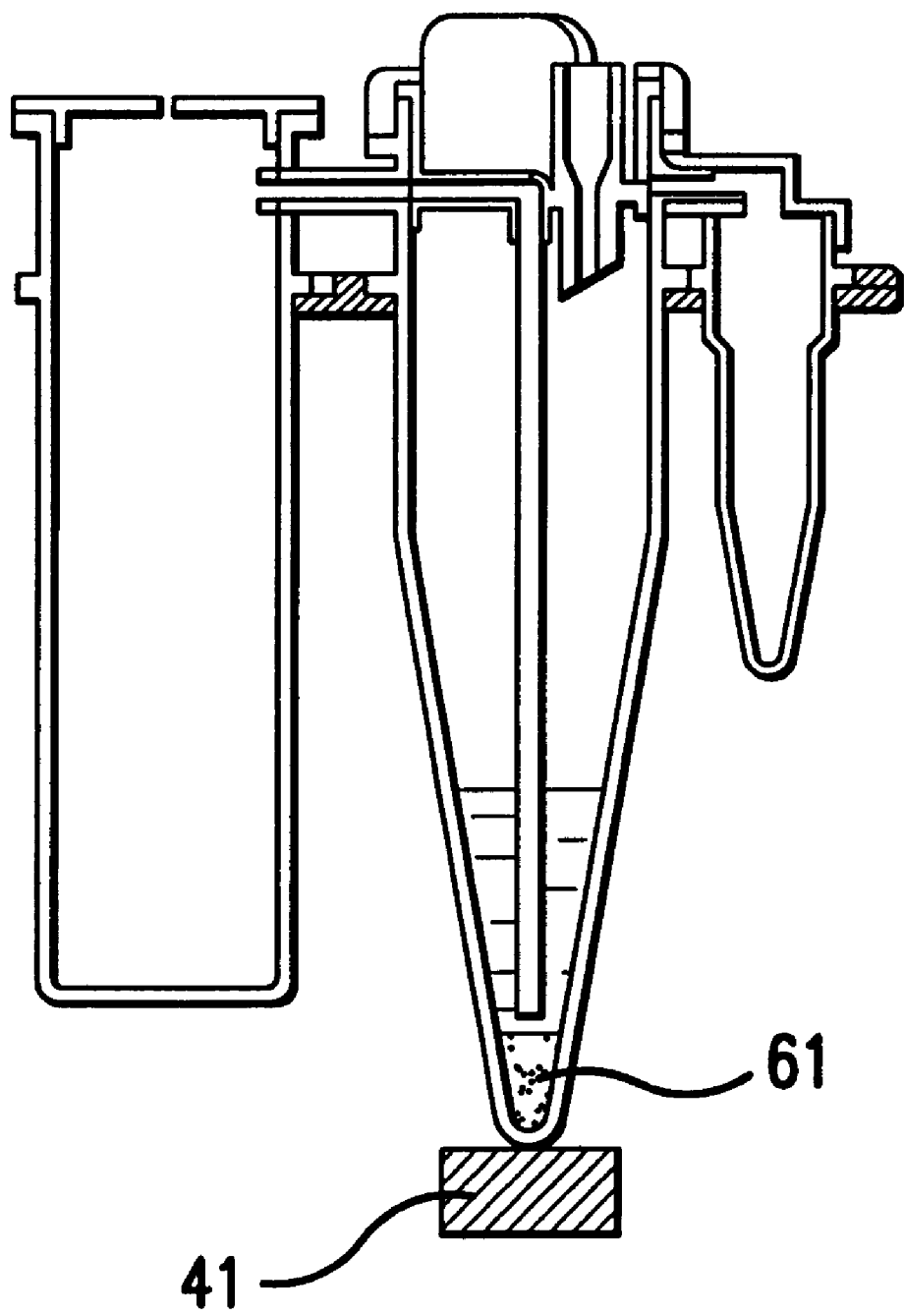
FIG. 13 is a schematic diagram illustrating a B/F separation step in the nucleic acid extraction procedure using the nucleic acid extraction apparatus of the invention, wherein the reference numerals 41 and 61 represent a permanent magnet and magnetic silica beads, respectively.

On completion of stirring, the vessel stand 13 is transferred, again by said transfer means, to position C where the holding means 17 is located (FIG. 5b). The vessel stand remains stationary in this position and the next step, i.e. B/F separation, is carried out. This status is shown in FIG. 13. The permanent magnet 41 of the holding means contacts the exterior bottom of the reactor tube 1 of the extraction vessel, whereby the magnetic silica beads 61 in the reactor tube 1 are retained in the bottom area of the reactor tube.

Figure 14:
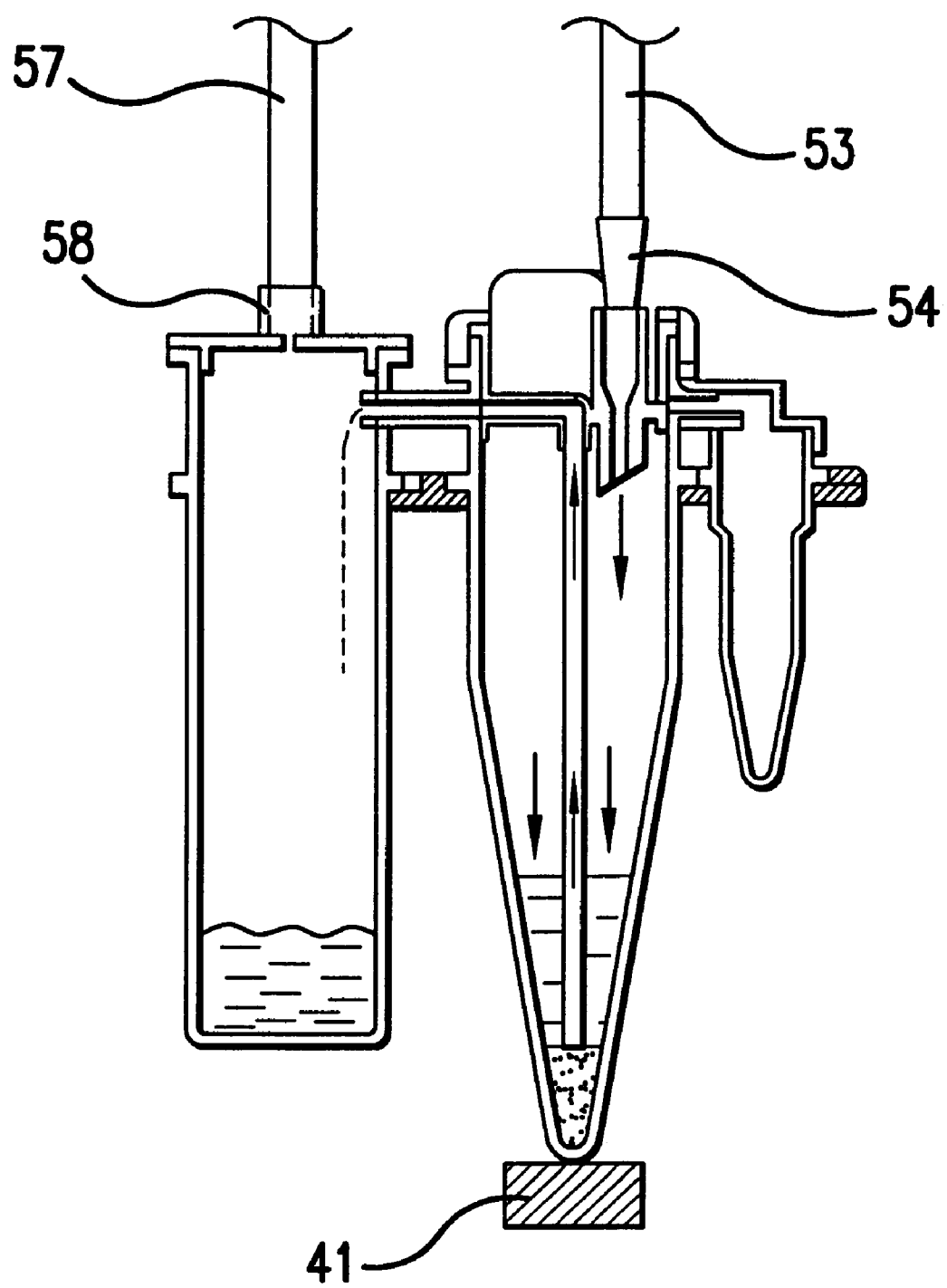
FIG. 14 is a schematic diagram illustrating a step of discharging an unwanted component solution in the nucleic acid extraction procedure using the nucleic acid extraction apparatus of the invention, wherein the reference numeral 41 represents a permanent magnet, 53 and 54 represent a pressure nozzle and a pad, respectively, and 57 and 58 an exhaust nozzle and a pad, respectively.

Furthermore, in this position C, the discharging means 16 is set above the extraction vessel and the next step, i.e. discharge of the unwanted component solution, is carried out. Thus, with the B/F separation being performed as shown in FIG. 13, the pressure nozzle 53 and exhaust nozzle 57 constituting the discharging means descend into engagement with the piercing pipe 10 and the hole of the cover 7, respectively, of the extraction vessel. This status is shown in FIG. 14.

As shown in FIG. 9, the pad 54 fitted to the forward end of the pressure nozzle 53 is inserted air-tight into the inlet of the reactor tube 1, that is to say the piercing pipe 10, and the pressurized air from a pump (not shown) is blown into the reactor tube 1. As a result, the unwanted component solution in the reactor tube 1 is discharged into the drain cup 2 through the discharge passageway comprised of the discharging pipe 5, valve passageway 11, etc. At the same time, the air introduced under pressure into the drain cup 2 is exhausted through the hole in the cover 7 on the drain cup and the passageway constituted by the exhaust nozzle 57. This series of B/F separation and discharge of the unwanted component solution is performed in position C.

Upon completion of discharge of the unwanted component solution, the discharging means 16 and holding means 17a return to a given position. On the other hand, the vessel stand 13 moves again to position A for introduction of the next solution (wash solution) into the reactor tube 1 and stops there (FIG. 5b), In accordance with the flow-chart shown in FIG. 10, the washing step is now carried out.

Introduction of the wash solution is performed by the distribution means 14 which serially dispenses the wash solution into the reactor tubes 1 of extraction vessels arranged on the vessel stand 13. As shown in FIG. 6, the pad 35 fitted to the forward end of the distribution nozzle 34 is inserted liquid-tight into the inlet of the reactor tube (the piercing pipe 10) and the reagent solution (wash solution) is introduced from the bottle 18 into the reactor tube 1 through the tube 30. Upon completion of dispensing into one extraction vessel, the distribution means 14 moves to the next extraction vessel and dispenses the wash solution in the same manner. Upon completion of dispensing into all the extraction vessels arranged on the vessel stand 13, the distribution means 14 returns to a given position and stops there.

The subsequent operations in the washing procedure, i.e. stirring, B/F separation, and discharge of the unwanted solution, may be performed in exactly the same manner as in the above extraction procedure. The washing procedure in nucleic acid extraction may vary, for example involving change of wash reagents or a plurality of washing cycles using the same reagent. In any case, the washing operations by the apparatus can be exactly the same as those described above.

The drying of the magnetic silica beads is now described.

Figure 15:
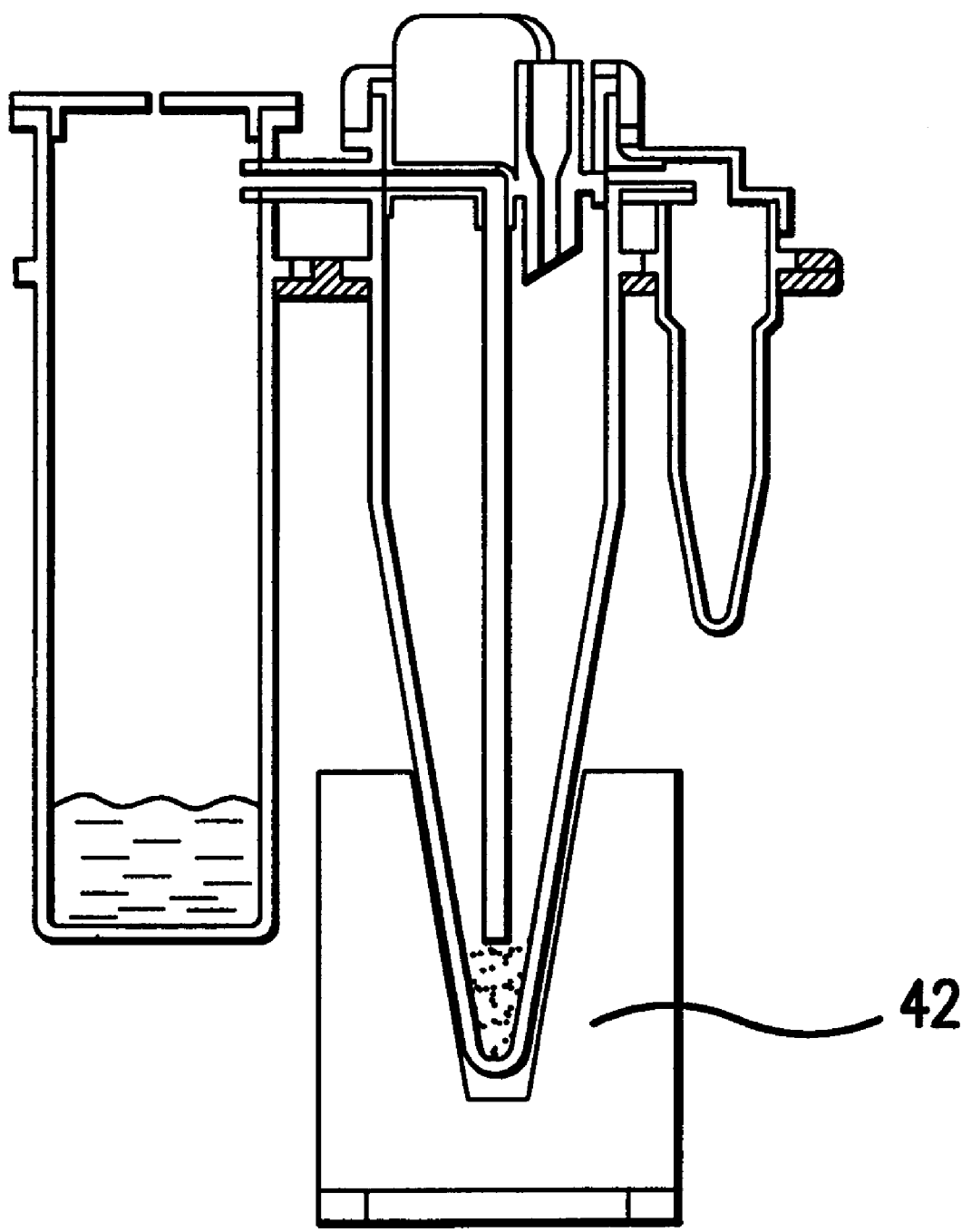
FIG. 15 is a schematic diagram illustrating a drying step or an eluent heating step in the nucleic acid extraction procedure using the nucleic acid extraction apparatus of the invention, wherein the reference numeral 42 represents a heating block.

Upon completion of discharge of the unwanted solution (washings) formed in the washing step, the vessel stand 13 is shifted to position D (FIG. 5b). Disposed in position D is the heating block 42 constituting the heating means 17b. As the heating block 42 ascends in response to rotation of the pole screw 48, the reactor tube 1 of the extraction vessel comes into contact with its recessed part and is heated. The drying is effected as the reactor tube is heated until the residual wash solution on the surface of the magnetic silica beads in the reactor tube have been completely evaporated off (FIG. 15).

Upon completion of drying, the distribution means 14 dispenses a solution of low ion concentration (eluent), such as sterilized water, into the reactor tube containing the magnetic silica beads and the solution is warmed for a definite time. This warming of the eluent is also performed by the heating block 42 disposed in position D (FIG. 5b). FIG. 15 shows this drying or eluent warming step.

Upon completion of warming of the eluent, the heating block 42 returns to a given position and the vessel stand 13 is shifted to position B where the stirring means 15 is disposed and the stirring is carried out.

Upon completion of stirring, the final nucleic acid recovery step is executed. For this purpose, the vessel stand 13 is shifted to position A where the distribution means 14 is located (FIG. 5b). Then, by the rotary arm 27 of the distribution means 14, the rotary element 6 mounted on the reactor tube 1 is rotated through 180 degrees. Thereupon, as illustrated in FIG. 4, the flow passageway constituted by the channel cover 8 of the recovery tube is brought into communication with the valve passageway 11 and discharging pipe 5 in the reactor tube 1 so that a preparation for recovery of the nucleic acid is completed. The above rotation of the rotary element is effected as the rotary arm grip 28 is engaged with the grip 12 of the rotary element 6 and the rotary arm 27 is driven by the motor 24. This rotation is serially carried out for one extraction vessel after another.

Figure 16:
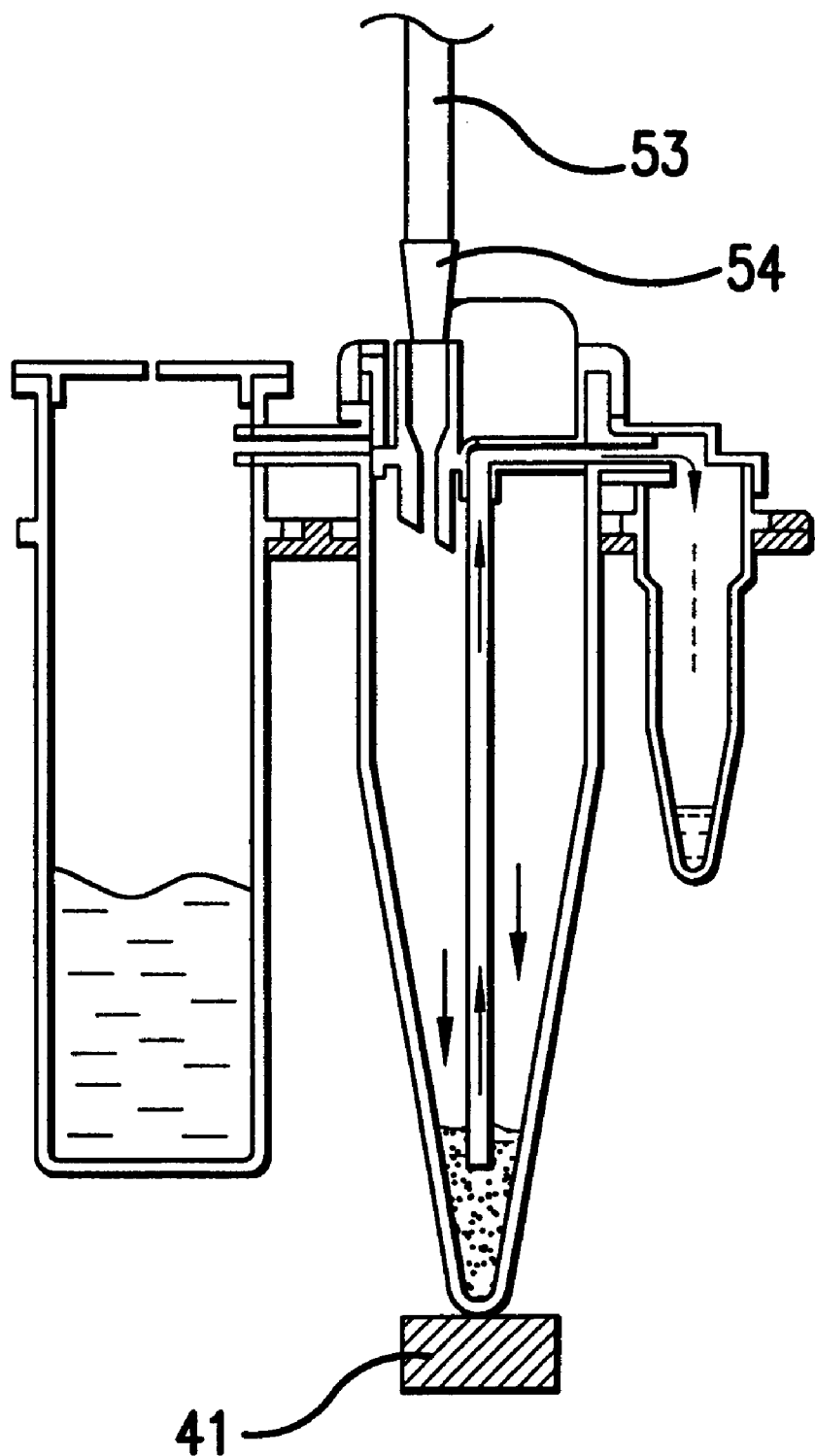
FIG. 16 is a schematic diagram illustrating a nucleic acid recovery step in the nucleic acid extraction procedure using the nucleic acid extraction apparatus of the invention, wherein the reference numeral 41 represents a permanent magnet and 53 and 54 represent a pressure nozzle and a pad, respectively.

Upon completion of rotation of the rotary element 6 for all the extraction vessels, the vessel stand 13 is shifted to position C where the holding means 17a is disposed (FIG. 5b). Here, as shown in FIG. 16, the magnetic silica beads are held stationary by the permanent magnet 41 for B/F separation and the pressurized air is introduced via the pressure nozzle 53 into the reactor tube 1. By this pressurization, the eluate containing the nucleic acid is discharged into the recovery tube 3 through the discharging pipe 5 and valve passageway 11 to recover the nucleic acid.

Upon completion of this recovery, the vessel stand 13 is shifted from position C to a given initial position, whereby the entire nucleic acid extraction procedure is completed and the apparatus stops its actions. Then, the operator takes out the extraction vessels from the vessel stand 13, disconnect the recovery tubes 3, and preserves them in the refrigerator or otherwise takes the necessary procedure.

The nucleic acid extraction procedure using the nucleic acid extraction apparatus of the invention has by now been described.

As mentioned hereinbefore, the extraction vessel and nucleic acid extraction apparatus of this invention are the vessel and apparatus well-suitable with the nucleic acid extraction technology utilizing a nucleic acid-binding magnetic carrier and, therefore, are simple and compact as compared with the system utilizing a centrifuge or a vacuum pump.

Furthermore, since in the apparatus of the invention the respective steps in the nucleic acid extraction procedure (dispensing of solutions, stirring, discharging and heating steps) are carried out at the definite positions for the means (distribution means, stirring means, discharging means and heating means) with one-to-one correspondence, by transferring extraction vessels serially thereto, the complicated extraction procedure can be carried through with high reliability, without risks for contamination, rapidly, and with high efficiency.

Moreover, since the extraction vessel of this invention is not open to the external atmosphere, the risk for contamination due to vessel-to-vessel carryovers is avoided so that highly dependable results can be expected. In addition, when the extraction vessels are disposable vessels, the cleaning operation can be omitted to avoid the risk for contamination by wash residues and the risk for infection with the viruses which biological samples may contain.

The apparatus of this invention thus features high dependability and safety.

Therefore, in the field of clinical examinations for genetic diagnosis where a large number of samples must be dealt with at one time as well as in the field of basic research, the present invention providing a nucleic acid extraction apparatus of great utility value with which nucleic acid components can be extracted rapidly, expediently, safely, and with high dependability.

What is claimed is:

1. A method for nucleic acid extraction using the nucleic acid extraction apparatus comprising
    (1) a group of extraction vessels each comprising a reactor tube in which a sample, a reagent solution and a magnetic carrier are admixed and reacted, a drain cup for pooling an unwanted component solution and a nucleic acid recovery tube, all as secured to a supporting plate,
    (2) a distribution means for dispensing a sample or other solution into each of said extraction vessels,
    (3) a stirring means for stirring the sample solution and magnetic carrier within the the reactor tube into the the drain cup or the nucleic acid recovery tube,
    (4) a holding means for holding said magnetic carrier stationary within the reactor tube in a position within the extraction vessel,
    (5) a discharging means for discharging the sample solution from thereactor tube into the drain cup or nucleic acid recovery tube while said magnetic carrier is held stationary within the reactor tube,
    (6) a heating means for heating the sample solution containing the magnetic carrier in said extraction vessel, and
    (7) a transfer means for transferring said extraction vessel to the required positions where said distribution means, stirring means, holding means, discharging means,and heating means are respectively disposed, wherein said method comprises
    (a) a step of extracting a nucleic acid from a sample and causing it to be adsorbed on a magnetic carrier in a reactor tube of an extraction vessel;
    (b) a step of separating the magnetic carrier carrying the nucleic acid adsorbed thereon from the solution;
    (c) a step of washing the separated magnetic carrier;
    (d) a step of eluting the nucleic acid from the magnetic carrier, and
    (e) a step of recovering the nucleic acid.

2. A method for nucleic acid extraction according to claim 1 wherein said (a) extraction step, (c) washing step, and (d) elution step are carried out by introducing an extraction solution, a wash solution, and an eluent, respectively, into the reactor tube containing the magnetic carrier by using the distribution means and then stirring the mixture by using the stirring means.

3. A method for nucleic acid extraction according to claim 1 wherein said (b) magnetic carrier separation step and (e) nucleic acid recovery step comprise discharging the solution from the reactor tube into the drain cup and nucleic acid recovery tube, respectively, by using the discharging means while the magnetic carrier is retained stationary within the reactor tube by using the holding means.

4. A method for nucleic acid extraction according to claim 1 wherein said (d) nucleic acid elution step comprises drying the magnetic carrier carrying the nucleic acid adsorbed thereon by using the heating means, introducing an eluent into the reactor tube containing said magnetic carrier by using the distribution means, stirring the magnetic carrier in the eluent by using the stirring means, heating the solution by using the heating means, and stirring it by using the stirring means again.

* * * * *